United States Patent [19]

Graham et al.

[11] Patent Number: 5,096,896

[45] Date of Patent: Mar. 17, 1992

[54] SUSTAINED RELEASE COMPOSITIONS

[75] Inventors: Neil B. Graham, Bearsden, Scotland; Robert E. Howells, Birkenhead, England; David A. Wood, Carluke; Koritala P. Rao, Glasgow, both of Scotland

[73] Assignee: National Research Development Corporation, London, England

[21] Appl. No.: 296,418

[22] Filed: Jan. 10, 1989

Related U.S. Application Data

[63] Continuation of Ser. No. 808,239, Dec. 13, 1985, abandoned, which is a continuation of Ser. No. 715,759, Mar. 25, 1985, abandoned, which is a continuation of Ser. No. 430,362, Sep. 30, 1982, abandoned.

[30] Foreign Application Priority Data

Sep. 30, 1981 [GB] United Kingdom ............ 8129574
Sep. 16, 1982 [GB] United Kingdom ............ 8226354

[51] Int. Cl.$^5$ ............... A61K 31/495; A61K 31/74
[52] U.S. Cl. ............................................. 514/157
[58] Field of Search .............. 514/169, 275, 573, 157; 528/361

[56] References Cited

U.S. PATENT DOCUMENTS

| 3,318,846 | 5/1967 | Smith et al. | 526/330 |
|---|---|---|---|
| 3,728,452 | 4/1973 | Haber et al. | 514/157 |
| 4,031,214 | 6/1977 | Easterbrook | 514/157 |
| 4,130,639 | 12/1978 | Shalaby et al. | 514/169 |
| 4,221,799 | 9/1980 | Graham | 424/78 |
| 4,328,209 | 5/1982 | Wasserman et al. | 514/179 |
| 4,438,258 | 3/1984 | Graham | 524/593 |
| 4,528,365 | 7/1985 | Graham | 528/361 |
| 4,584,188 | 4/1986 | Graham | 424/19 |
| 4,645,781 | 2/1987 | Koleske et al. | 528/361 |
| 4,696,921 | 9/1987 | Merkli | 514/157 |
| 4,814,182 | 3/1989 | Graham et al. | 424/484 |
| 4,882,166 | 11/1989 | Graham et al. | 424/462 |

FOREIGN PATENT DOCUMENTS

| 0000291 | 1/1979 | European Pat. Off. |
| 2336936 | 7/1977 | France |
| 991970 | 5/1965 | United Kingdom |
| 1089871 | 11/1967 | United Kingdom |

OTHER PUBLICATIONS

Yunker J.C.S. Chem. Comm., 1975.

Primary Examiner—Shep K. Rose
Attorney, Agent, or Firm—Oblon, Spivak, McClelland, Maier & Neustadt

[57] ABSTRACT

A non-crosslinked derivative formable by reacting at least one substituted or unsubstituted, saturated or unsaturated, mono-, di- or poly-carboxy, hydroxy or mercapto hydrocarbon with at least one cyclic unsaturated (thio)ether.

16 Claims, No Drawings

SUSTAINED RELEASE COMPOSITIONS

This application is a Continuation of application Ser. No. 06/808,239, filed on Dec. 13, 1985, now abandoned, which is a continuation of abandoned application Ser. No. 06/715,759 filed Mar. 25, 1985, which is a continuation of abandoned application Ser. No. 06/430,362 filed Sept. 30, 1982.

This invention relates to derivatives suitable for use as diluents; more particularly, but not exclusively, this invention relates to derivatives which are desirably liquids suitable for use as injectable diluents, particularly for materials having biological activity. This invention also relates to compositions, particularly sustained release compositions, comprising them and an active, especially biologically active, substance.

A defect or oral dosage forms of medication is patient failure; that is, the failure of the patient properly to adhere to the complete oral administration schedule prescribed. This failure is exacerbated for extended prescription and for prophylactic, rather than therapeutic, treatment. To overcome this defect, attempts have been made to administer materials having biological activity, for example drugs, as a subcutaneous implant, for example in the abdominal wall, or as an injectable preparation. This latter has the advantage that it can be administered by paramedical personnel.

It is also desirable that injectable preparations should be long acting. Diluents for such preparations should be neutral and stable; in particularly, they should not react with the materials having biological activity to form toxic products. Also, they should not be too viscous readily to pass through a hypodermic needle. Moreover, they should be inert and non-irritating to the tissue at the injection site; be essentially free from antigenic properties and be rapidly absorbed from the injection site soon after the medication period is terminated leaving no residue.

Mineral oils have been used as a diluent in intramuscular injection, for example of steroid hormones, but they can on occasion give rise to painful local reactions including anaphylactic irritation; moreover, the toxicological testing required for mineral oil preparations is both extensive and expensive. Silicone fluids have been used as diluents but it is found that compositions comprising them lose their efficacy comparatively rapidly, for example in about three weeks.

The present invention seeks to provide a diluent composition which overcomes, or reduces, at least some of the above-mentioned disadvantages.

According, therefore, to a first aspect of this invention, there is provided a derivative which is a monomeric adduct or thermoplastic polymer formable by adding:
(a) at least one monomeric or polymeric, substituted or unsubstituted, saturated or unsaturated, mono-, di- or poly-acid, neutral or amphoteric active hydrogen atom-containing organic compound to the, or at least one of the, ring double bonds of
(b) at least one mono-, di- or poly-unsaturated cyclic (thio) ether.

By "Unsaturated cyclic (thio)ether" is meant herein a compound comprising at least one $>C=C-O-$ or $>C=C-S-$ group wherein the or each oxygen (or sulphur) atom is a hetero atom and the or each double bond conjugated therewith is contained in the hetero ring.

Apart from the active hydrogen atom-containing functional group, the organic compound (a) may be substituted, for example by one or more halogen, such as chlorine or bromine, atoms. Desirably, the substituent should not be basic and it is generally convenient to utilise unsubstituted organic compounds (a).

The organic compound (a) may be aliphatic, alicyclic or aromatic and may comprise olefinic unsaturation. It is generally convenient to utilise aliphatic, preferably saturated aliphatic, organic compounds (a); for example, mono-, di- or poly-carboxy, hydroxy, amido or mercapto group-containing organic compounds, preferably mono- or di-carboxy or hydroxy group-containing organic compounds.

The organic compound (a) may be monomeric. Where the derivative of this invention is formable from a monomeric organic compound (a), that organic compound is preferably a mono- (or di-) carboxy or hydroxy $C_1$ (or $C_2$) to $C_{10}$ aliphatic hydrocarbyl(ene), preferably a $C_2$ to $C_4$ alkan (di) ol.

The organic compound (a) may be polymeric, Where the derivative of this invention is formable from a polymeric organic compound (a), that organic compound is preferably a mono-, di- or poly- hydroxy homo- or co-poly ($C_3$ to $C_5$ alkylene oxide).

A mixture of a plurality of monomeric organic compounds (a) or of a plurality of polymeric organic compounds (a) or of at least one monomeric with at least one polymeric organic compound (a) may be used.

Examples of mono-carboxy or hydroxy hydrocarbyls(a) include monocarboxylic acids, phenols and alcohols, desirably those with less than 18, preferably less than 10, carbon atoms; for example, formic, acetic, propionic, butyric and valeric acids, benzoic and phenylacetic acids; phenol and cresols; methanol, ethanol, propanol, butanol and n-octanol. Alcohols are most suitable, especially the $C_1$ to $C_6$, preferably $C_2$ to $C_4$, alcohols.

Mixtures of monocarboxylic acids, phenols and alcohols may be used. Preferably the monocarboxylic acids, phenols and alcohols are linear.

Examples of di-carboxy or hydroxy hydrocarbylenes (a) including dicarboxylic acids, dihydric phenols, hydroxyacids and glycols, desirably those with less than 18, preferably less than 10, carbon atoms; 1,2-cyclohexanedicarboxylic, 1,3-cyclohexanedicarboxylic and 1,4-cyclohexanedicarboxylic acids, phthalic, isophthalic and terephthalic acids, 4,4'-dihydroxyphenol-2,2-propane, resorcinol, quinol and orsinol, lactic, 2-hydroxyisobutyric, 10-hydroxydecanoic, 12-hydroxyoctadecenoic, 12-hydroxy-cis-9-octadecenoic, 2-hydroxycyclohexane carboxylic, 2-hydroxy-2-phenyl (D) propionic, dephenylhydroxyacetic, 2-hydroxybenzoic, 3-hydroxybenzoic and 4-hydroxybenzoic acids, glycol, propanediols and butanediols. Glycols are most suitable, especially the $C_2$ to $C_6$, preferably $C_2$ to $C_4$ glycols. Mixtures of dicarboxylic acids, dihydric phenols, hydroxy acids and glycols may be used. Preferably the dicarboxylic acids, dihydric phenols, hydroxy acids and glycols are linear.

Examples or organic compounds (a) substituted by more than two carboxy or hydroxy groups include polycarboxylic acids, polyhydric phenols, hydroxy acids and polyhydric alcohols, desirably those with less than 18, preferably less than 10, carbon atoms; for example aliphatic polyols such as glycerol, erythritol, pentaerythritol, sorbitol, dulcitol, inositol, 2-ethyl-2-hydroxymethylpropane-1,3-diol and 1,2,6-hexanetriol; aromatic polyols such as 1,2,3-trihydroxybenzene, 1,2,4-trihydroxybenzene, 1,3,5-trihydroxybenzene; araliphatic polyols; hydroxy aliphatic, alicyclic and aromatic carboxylic acids, including Krebs cycle acids, such as citric acid, malic acid, tartaric acid, 2-hydroxy-3-methyl (D) succinic acid, ascorbic acid, 2,3-dihydroxybenzoic acid, 2,4-dihydroxybenzoic acid, 2,5- dihydroxybenzoic acid, 2,6-dihydroxybenzoic acid, 2,3,4-trihydroxybenzoic acid, 2,4,5-trihydroxybenzoic acid, b 2,4,6-trihydroxybenzoic acid and 3,4,5-trihydroxybenzoic acid. Mixtures of polycarboxylic acids, polyhydric phenols, hydroxy acids and polyhydric alcohols may be used. Preferably the polycarboxylic acids, polyhydric phenols, hydroxy acids and polyhydric alcohols are linear.

Mixtures of mono-, di- and poly-substituted organic compounds (A) may be used to obtain the desired rheological and release properties in the diluent composition.

Desirably the mono-, di- or poly-unsaturated cyclic (thio)ether (b) has the formula:

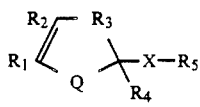

in which:

$R_1$, $R_2$ and $R_4$, which may be the same or different, each represent a hydrogen atom or a substituted or unsubstituted hydrocarbyl or hydrocarbyloxy group;

$R_3$ represents a substituted or unsubstituted methylene, ethylene or 1,3-propylene group;

$R_5$ represents a monovalent group reactive with the organic compound (a) or a hydrogen atom or a $C_1$ to $C_4$ alkyl group;

Q represents an oxygen or a sulphur atom; and

X represents:

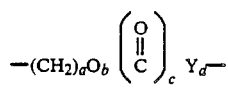

in which:

Y represents an oxygen atoms or an —$NR_6$— group wherein $R_6$ represents any of the values which $R_1$ may assume;

A is 0 or 1;

b is 0 or 1;

c is 1 or 2;

d is 0 or 1;

with the proviso that at least one of b or d is 1.

X may, as shown, represent any hydrolysable carboxylic acid ester, carbonate ester or oxalate ester function, or an amide analogue. Preferably, however, X represents —COO— or —$CH_2$OCO—.

Particularly preferred cyclic unsaturated ethers have the formula:

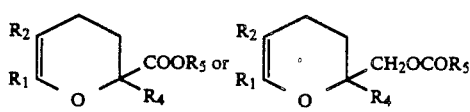

in which:

$R_1$, $R_2$ and $R_4$, which may be the same or different, and $R_5$ are as herein defined. $R_5$ may suitably represent any group provided that it is reactive with the organic compound (a). Preferred examples are vinyl (thio)ether and epoxy groups.

It is particularly preferred that $R_5$ represents a group derived from a cyclic unsaturated vinyl (thio)ether, especially of the formula:

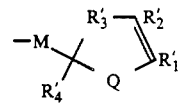

in which:

$R_1'$, $R_2'$, $R_3'$ and $R_4'$, which may be the same or different, represent any of the values which $R_1$, $R_2$, $R_3$ and $R_4$ may assume;

M represents the group —$ZX'$—;

Q' represents an oxygen or sulphur atom;

X' represents any of the values which X may assume; and

Z represents a single bond or a carbon-linked mono-, oligo- or homo- or co- poly(substituted or unsubstituted hydrocarbylene or hydrocarbyleneoxy) residue, such as a substituted or unsubstituted arylene, alkylene or alkylene oxide residue.

Especially preferred cyclic unsaturated ethers are the reaction products formed by subjecting one or a mixture of dihydropyran aldehydes to disproportionation by the Tischenko reaction; they have the formula:

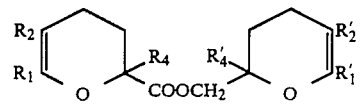

in which:

$R_1'$, $R_2'$ and $R_4'$, which may be the same or different, represent any of the values which $R_1$, $R_2$ and $R_4$ respectively may assume. A preferred such compound is acrolein tetramer (in which the $R_i$ all represent hydrogen atoms).

Cyclic unsaturated ethers wherein X comprises a —COO— or —$CH_2OCO$— group may conveniently be prepared from the tetramer of the corresponding unsaturated aldehyde produced by the Tischenko reaction; namely:

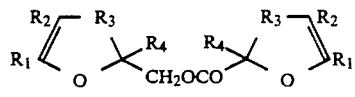

Thus, cyclic ethers wherein X comprises a —COO— group may be prepared by reaction of the tetramer with an alcohol $R_5OH$ using a transesterification catalyst and reaction conditions:

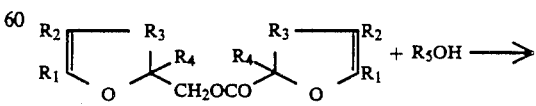

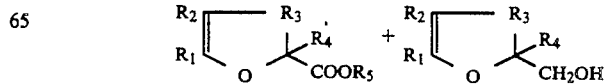

Cyclic ethers wherein X comprises a —CH$_2$OCO— group may be prepared by reaction of the tetramer with a lower alkyl carboxylic acid ester R$_5$COO R$_7$ in which R$_7$ represents a lower alkyl group using a transesterification catalyst and reaction conditions:

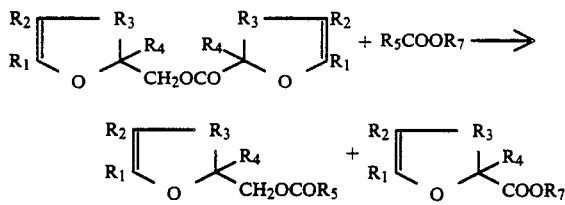

The respective by-products may also be transesterified with R$_5$COO R$_7$ or R$_5$OH to give, correspondingly:

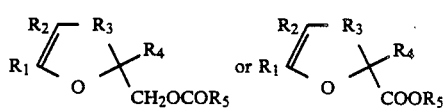

The corresponding amides may be prepared analogously.

Cyclic ethers where X comprises a —COO— group may also be obtained by mild oxidation of the dimer of the corresponding unsaturated aldehyde, followed by esterification of the salt, for example the silver salt.

Meta-carbonates and oxalates may be obtained, respectively by esterification:

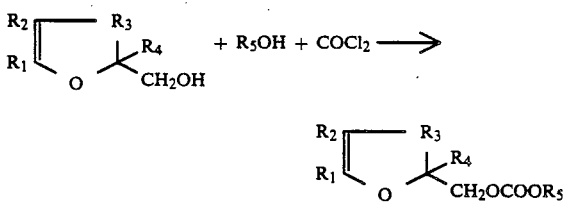

(Chloroformic esters, such as ethyl chloroformate, may also be used).

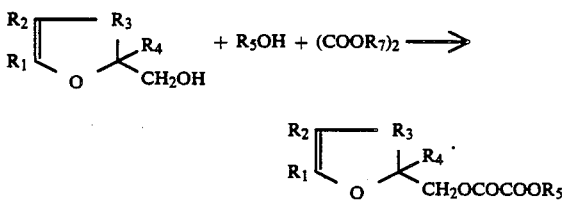

It is, however, to be stressed that acrolein tetramer is readily prepared from acrolein which is a commercially available material; can readily be purified; and has been found to be satisfactory in the practice of this invention.

Particularly preferred derivatives of the invention are those wherein the derivative has the formula:

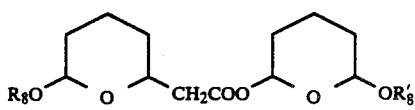

in which:

R$_8$ and R'$_8$, which may be the same or different, each represent a C$_1$ to C$_6$ alkyl group, a C$_2$ to C$_6$ hydroxyalkyl group or a homo- or co- poly(propylene or butylene oxide).

The mono-, di- or poly-unsaturated cyclic (thio)ether (b) may also desirably have the formula:

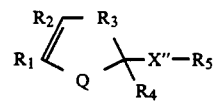

in which:

R$_1$, R$_2$, R$_3$, R$_4$, and R$_5$ and Q are as hereinabove defined; and X" represents:

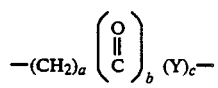

in which:

Y represents an oxygen atom or an —NR$_6$— group wherein

R$_6$ represents any of the values which R$_1$ may assume;
a is 0 or 1;
b is 0 or 1;
c is 0 or 1;
with the proviso that b+c is 1.

the mono-, di- or poly-unsaturated cyclic(thio)ether (b) may also comprise the aldol condensation product of at least one dimer of the corresponding unsaturated aldehyde:

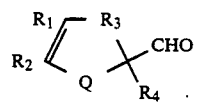

namely:

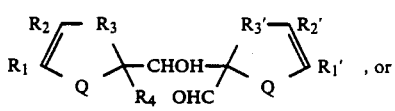, or

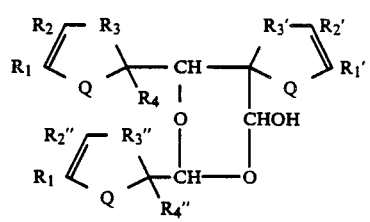

The mono-, di- or poly-unsaturated cyclic (thio)ether (b) may further comprise the Diels-Alder product of reacting at least one unsaturated aldehyde with a polyvinyl ether of a polyhydroxy compound:

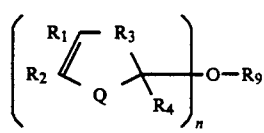

wherein:

$R_9$ represents an n-valent hydrocarbon or poly(oxyhydrocarbon) residue of an n-hydroxy compound.

The polymerisable cyclic (thio)ether (i) may further comprise

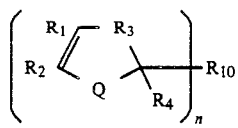

wherein:

$R_{10}$ represents an n-valent non-hydrolysable bridging residue.

These last four depicted compounds give rise to compositions of the invention which are less readily hydrolysed. Their use gives a first method for providing a controlled release composition according to the invention with a desired rate of hydrolysis.

The degree of hydrolytic stability provided can also be accurately tailored by a number of other different mechanisms. Thus, homologues or acrolein tetramer, for example methacrolein tetramer or the mixed acrolein/methacrolein tetramer, exert steric hindrance, which increases as the size of $R_4$ increases, to the hydrolysable ester or amide function X and thereby increases the stability of the derivative. Mono-, di and poly-carboxy and phenolic hydroxy substituted hydrocarbons form derivatives which are prone to hydrolysis and which yield catalytic acidic species thereon; derivatives wherein X and X', which may be the same or different, each represent a —COO— or —CH$_2$OCO— group and X represents a substituted or unsubstituted hydrocarbylene group also facilitate hydrolysis. Examples include:

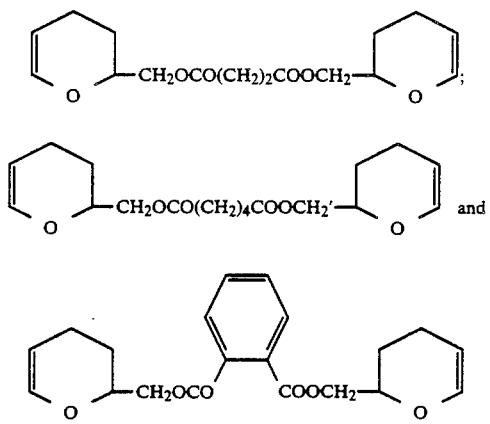

Furthermore, derivatives which retain one or more carboxy or hydroxy groups comprise a relatively high level of water which itself facilitates hydrolysis.

The groups $R_1$, $R_2$ and $R_4$ may each represent a substituted or unsubstituted hydrocarbyl or hydrocarbyloxy group: examples include unsubstituted or halosubstituted $C_1$ to $C_4$ alkyl, such as methyl or ethyl; unsubstituted $C_6$ to $C_{10}$ aryl or arakyl such as phenyl or benzyl; and oxy analogues. In the case of $R_4$, increase in the size of the group increases the steric hindrance to any hydrolysable ester or amide function and thereby increases the stability of the hydrogel. It is preferred, however, from the standpoint of ease of preparation and availability, that at least one, and preferably all, or $R_1$, $R_2$ and $R_4$ represents a hydrogen atom. The group $R_3$ may represent a mono- or poly-substituted ethylene group, preferably an unsubstituted ethylene group; that is, a dihydro(thia)pryan derivative.

Preferred such compounds (i) are ethers; that is, those compounds of the above formula wherein Q represents an oxygen atom, especially dihydropyrans.

A proportion of polyethylene glycol of the formula $R_{11}$—(OCH$_2$CH$_2$)$_n$—OH wherein $R_{11}$ represents a hydrogen atom or an alkyl group and n is a number such that the number average molecular weight, $\overline{M}_n$, is less than 1000 may also be incorporated to facilitate hydrolysis.

The derivatives formed by reacting acrolein tetramer and $C_1$ to $C_{12}$ monohydric alcohols are oils or relatively high boiling point and low vapour pressure at ambient temperature. They have a relatively low viscosity (typically 11–300 cP at 20° to 25° C.) which allows their administration by injection and, on cooling below $-20°$ C., form colourless glasses. Their densities at 20° C. are close to that of water with a progressive decrease as the alkyl chain length is increased. They are insoluble in water and body fluids.

While it is preferred, in accordance with this invention, that the derivative is a liquid at a temperature from 35° C. to 40° C. and at standard pressure, solids are of interest as implant materials and in co-precipitation with active substances.

Both solid and liquid derivatives may be extended with pharmaceutically-acceptable oils, such as olive oil and also with other derivatives of the invention of lower molecular weight in order to increase their plasticity or decrease their viscosity, and to alter the release properties of a sustained release composition formed therefrom.

In accordance with a preferred feature of this invention, there is provided a derivative which is a monomeric adduct and wherein the molar ratio of (a) to (b) is no greater than N:1 wherein n is the number of ring double bonds in (b). There is also provided a derivative which is a thermoplastic polymer and wherein the molar ratio of (a) to (b) is no less than $(n-1):1$ wherein n is the number of ring double bonds in (b) and $N>1$. Preferably, the derivative is formed by the reaction of (a) with (b) in the presence of a Bronsted or Lewis acid.

In accordance with a further aspect of this invention, there is provided a composition which comprises a derivative as herein described and an active substance, particularly a biologically active substance. It is preferred that the active substance is intimately admixed with the derivative as a suspension, dispersion or solution. The active substance may be presented as a controlled release composition in accordance with our copending application [121641, filed on even date herewith] suspended in a derivative of this invention.

Such compositions may, for example on injection, provide a timed release (typically 1 to 7 days) of active substance from a depot. It is preferred, however, that such compositions provide a sustained release of active substance for 1 to 3 months or even longer. These differing rates of release may be brought about by tailoring the derivative as aforesaid or by forming a pro-drug as is hereinafter described.

The present invention is of broad applicability in the formulation of active substances, particularly, but not exclusively, biologically active substances releasable at a sustained rate. Examples of classes of biologically active substances which may be incorporated in the sustained release compositions of the present invention include flavourings, pharmaceuticals, bacteriostats, viruscides, pesticides such as insecticides, nematicides, molluscicides and larvicides, herbicides, fungicides, algaecides, topical or dermatological agents, antifoulants for marine growth prevention, proteins, for example enzymes, peptides, microbiological and plant hydroculture salts and nutrients and preservatives, veterinary trace metal formulations, and other growth promoting factors used in animal husbandry: for example, antianaemia preparation and anabolic steroids. Of particular interest are compositions of the present invention comprising, as biologically active substance, at least one pharmaceutical.

The compositions of this invention thus find wide application in medical and surgical, including veterinary, contexts and in horticulture and agriculture as well as outside these areas.

Specific classes of drug which may be utilised in a sustained release composition of the invention include abortifacients such as prostaglandins, hypnotics, sedatives, tranquilisers, antipyretics, anti-inflammatory agents, preparation for the treatment of allergies, for example anti-histamines, anti-tussives, anticonvulsants, muscle relaxants, anti-tumour agents, for example those for the treatment of malignant neoplasia, local anaesthetics, anti-Parkinson agents, topical or dermatological agents, diuretics, for example those containing potassium, such as potassium iodide, preparations for the treatment of mental illness, for example preparations containing lithium for use in the treatment of manic depression or containing prostaglandins for the treatment of schizophrenia, anti-spasmodics, anti-ulcer agents, preparations containing various substances for the treatment of infection by pathogens including antifungal agents, for example metronidazole, anti-parasitic agents and other anti-microbials, anti-malarials, cardiovascular agents, preparations containing hormones, for example androgenic, estrogenic and progestational hormones, notably steroids such as oestradiol, sympathomimetic agents, hypoglycaemic agents, contraceptives, nutritional agents, preparations containing enzymes of various types of activity, for example chymotrypsin, preparations containing analgesics, for example aspirin, and agents with many other types of action including nematocides and other agents of veterinary application. Mixtures of active substances may be incorporated into the sustained release composition.

The sustained release compositions of this invention may be used as a contraceptive composition suitably containing, as active substance, at least one natural or synthetic steroid sex hormone for example an estrogen or progestogen. Suitably progestogens include the natural progesterone and its synthetic analogues, including 11-dehydroprogesterone, delalutin, 21-fluoro-17-acetoxy-6-α- methylprogesterone, medroxyprogesterone acetate, megestrol acetate, chlormadinone acetate, ethisterone, dimethisterone, A-norprogesterone, 19-norprogesterone, 21-norprogesterone, normethandrone, norethynodrel, norethindrone and its acetate, Dl- and D-norgestrel, norgestrienone, ethynodiol diacetate, lynstrenol, ethynylestradiol, retroprogesterone, dydrogesterone, norvinodrel, quingestranol acetate, norethisterone and its acetate and oenanthate, anagesterone acetate, medrogestone, clomagestone, allyl estrenol and cingestol, preferably progesterone. Suitably oestrogens include the natural β-oestradiol and its synthetic analogues, principally ethinyloestradiol or mestranol, preferably β-oestradiol.

The sustained release compositions of this invention are also useful in the treatment of diabetes and pernicious anaemia where, for example, the controlled release of insulin and cobalamin, respectively may be utilised.

Moreover, the sustained release compositions of this invention are particularly suited to treatment, both prophylactic and therapeutic, of tropical diseases; for example malaria, leprosy, schistosomiasis and clonorchiasis. Examples of drugs which can be used as biologically active substance in sustained release compositions of this invention for the treatment of these and other tropical diseases include quinine, sulphonamides, rifamcin, clofaximine, thiambutosine, chlorphenyl derivatives, chlorguamide, cycloguanil, pyrimethamine, sulphadiazine, trimethoprim, quinoline derivatives such as pamaquine, chloroquine, pentaquine, primaquine and amodiquine, pararosaniline, sulphametizole, quinacrine, dapsone, sodium sulphoxone, sulphetrone, sodium hydnocarpate and sodium chaulmoograte. Drugs of particular effectiveness are cycloguanil, pyrimethamine and sulphadiazine.

Anti-biotics, such as tetracycline (both as free base and hydrochloride or a mixture thereof), have also been found to be efficacious in the treatment of tropical disease in combinations according to this invention.

The sustained release compositions of this invention are also very well suited to veterinary applications. Examples include liquid depot preparations of antibiotics for general antibacterial activity and also in the treatment of anaplasmosis in cattle; preparations for provision of a wide spectrum of activity against both ectoparasites, for example termites and endoparasites including arthropods, arrested larvae stages of nematodes, lungworms and general strongyles: these may comprise avermectins; preparations for provision of activity against remotode, cestode and roundworm infections: these may comprise amoscanate and praxiquantel: preparations for provision of activity against theileria in cattle: these may comprise biologically active naphthoquinones such a s menoctone; preparations for provision of activity against babesiosis in cattle, horses and dogs: these may comprise berenil, amidocarb and diampron; preparations for provision of activity against liver fluke in sheep and cattle and against Hemonchus species: these may comprise closantel.

In accordance with a particularly preferred feature of this invention, there is provided a pro-drug composition wherein at least part of the organic compound (a) comprises a mono-, di- or poly-carboxy, hydroxy or mercapto-substituted biologically active compound.

Examples of such biologically active compounds include hydroxylated steroids, such as norethisterone or laevo-norgestrel; prostaglandins, such as $PGE_1$, $PGF_1\alpha$, $PGE_2$, $PGF_2\alpha$, $PGE_3$, $PGF_3\alpha$, 15-methyl $PGF_2$, 16,16-dimethyl-$PGE_2$, 16-phenoxy-17,18,19,20-tetramer-$PGE_2$, 16,16-dimethyl-trans-$\Delta^2$- PGE, and 16-(3-trifluoro methyl phenoxy)-17,18,19,20-tetranor-$PGF_2\alpha$; and acetylsalicyclic acid. Certain of the previously mentioned substituted hydrocarbons are themselves biologically active; for example alkyl phenols.

Where all of the organic compound (a) is a biologically active compound the pro-drug composition may be a solid. Where some, preferably at least an equimolar amount, of the organic compound (a) is a mono-, di- or poly-carboxy, hydroxy or mercapto-substituted hydrocarbon as aforesaid, for example a trihydric, dihydric or monohydric alcohol, and, preferably, where the aforesaid molar ratios apply, the pro-drug composition may be a hydrophobic or hydrophilic liquid. In this manner, not only may a solid biologically active compound be converted to a liquid formulation but it may also have its lyophilicity tailored to the pharmaceutical needs.

A solid pro-drug in accordance with the invention may be dissolved or dispersed in a derivative of the invention or in a mixture of such derivatives with each other and/or one or more conventional injectable diluents; for example olive oil. A liquid pro-drug in accordance with the invention may be master batched and then diluted with a derivative of the invention or with a mixture of such derivatives with each other and/or one or more conventional injectable diluents; for example olive oil. Liquid pro-drugs also act as surface active agents for their conjugate biologically active compound in the conjugate derivative. In this manner, substantial quantities of insoluble or poorly soluble biologically active compound may be homogeneously dispersed in derivatives according to this invention. Other biologically active compounds, and even other pro-drugs, may be incorporated in such compositions.

Where the biologically active compound comprises an amino or amido group, especially an aliphatic amino or amido group, and where the derivative comprises a carboxylic ester group, that ester group could be replaced by an amido group through which the biologically active compound is combined in a pro-drug. This may obtain even when all the substituted hydrocarbon is not a biologically active compound or when at least a part of the substituted hydrocarbon is the same or a different biologically active compound.

In accordance with a further aspect of this invention, there is also provided a sustained release composition as herein described for use in prophylactic, therapeutic or contraceptive methods of treatment of an animal or human patient.

This invention provides a method of prophylactic or therapeutic treatment of a human or animal patient such as for contraception, which comprises applying to the patient an effective dosage of a sustained release composition as herein described.

This invention also provides a process for the preparation of a derivative, especially a liquid diluent derivative, as herein defined, which process comprises reacting at least one monomeric or polymeric, substituted or unsubstituted, saturated or unsaturated, mon-, di- or poly- and, neutral or amphoteric active hydrogen atom-containing organic compound with at least one mono-, di- or poly-unsaturated (thio)ether in the presence of, if required, a Bronsted or Lewis acid.

The process of the invention may be effected at a temperature from −70° C. to 120° C., but advantageously the process is effected at an elevated temperature such as from 50° to 110° C., suitably from 60° to 100° C., especially from 70° to 90° C. Ambient or autogenous pressure may be used.

Suitable Bronsted and Lewis acids include strong mineral acids which are not redox reagents under the reaction conditions such as hydrochloric and sulphuric acid, tosylic acid, brosylic acid and the adduct of methanol and boron trifluoride. Suitable Lewis acids include boron trifluoride and its etherate, boron trichloride, boron tribromide, aluminium tetrachloride, aluminium tribromide, gallium trichloride, germanium tetrachloride, tin tetrabromide, zinc chloride and ferric chloride, ferric chloride being preferred. From 0.01% to 2%, particularly from 0.04% to 1%, based on the total weight of the reaction mixture may suitably be used.

Where the or each organic compound (a), for example a mono-, di- or poly-carboxy, hydroxy or mercapto hydrocarbon, is insoluble, as is often the case with poly-carboxylic acids, in the cyclic unsaturated (thio)ether, or mixture thereof, it is necessary to use a solvent, rather than mass, reaction theatre.

Where a plurality of organic compounds (a), for example mono-, di- or poly-carboxy, hydroxy or mercapto hydrocarbon, is used stoichiometry and addition sequence is important. For example, to prepare the ethyl propyl, or propyl butyl mixed acetal of acrolein tetramer it is preferred to react the acrolein tetramer with a equimolar amount of one of the alcohols (for example, the ethanol or propanol, respectively); and then react that product with a equimolar amount of the other alcohol.

Likewise, three moles of acrolein tetramer react with one mole of glycerol to give:

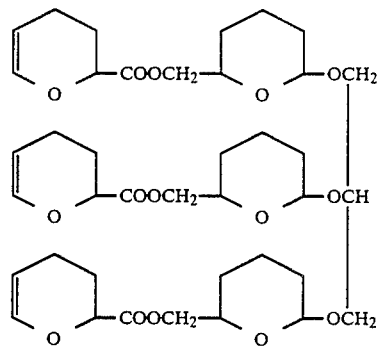

which can then be reacted with three moles of an alcohol to provide an oil of the invention.

Where the active substance comprises a free amino group, and is soluble in the reaction mixture, this can prevent the reaction. Where, therefore, such an active substance is incorporated in the composition before the process is completed it has either (a) to be rendered insoluble or (b) converted to a soluble quaternary ammonium salt, either or which may be effected in situ.

It may be desired to incorporate the active substance before the process is completed (c) where it is intended that the active substance, s the organic compound (a) is incorporated into the derivative as a pro-drug as aforementioned or (d) where the viscosity of the final composition would be too high to allow satisfactory dispersion of the active substance therein. In the latter case a quantity of base sufficient to neutralise the remaining acid or acid catalyst is added; the active substance admixed therewith; and the process continued with a fresh quantity of catalyst;

The following examples illustrate the invention.

Acrolein tetram (ex Canadian Industrial Ltd.) was carefully triple distilled under reduced pressure with a dry nitrogen bleed. That middle fraction which distilled between 78° and 80° C. was collected and sealed under an inert atmosphere into small glass ampoules ready for use in the Examples.

All liquid reactants which could be distilled without risk of decomposition were redistilled, collected and sealed under an inert atmosphere prior to use. Glycols were dried by being maintained, at ambient temperature, for 4 hours under reduced pressure with a dry nitrogen bleed and sealed under an inert atmosphere.

Anhydrous ferric chloride (ex Aldrich) was sublimed in a cold finger condenser to remove any trace water.

EXAMPLE 1

7.86 g of acrolein tetramer were added to 2.24 g of dried methanol (ex Aldrich) containing 0.1% w/w anhydrous ferric chloride. The mixture was then maintained in a sealed vessel at 70° C. for 1.5 hours.

A clear oil resulted which was qualitatively more viscous than the starting acrolein tetramer. The oil gave no characteristic >C=C< IR absorption at 1645 cm$^{-1}$ indicating that complete reaction of the acrolein tetramer double bonds had occurred.

EXAMPLE 2

38.85 g of acrolein tetramer were added to 11.10 g of dried methanol containing 0.1% w/w anhydrous ferric chloride. The mixture was then maintained in a sealed vessel at 75° C. for 2.5 hours.

A clear, orange oil resulted which gave no characteristic >C=C< IR absorption at 1645 cm$^{-1}$.

EXAMPLE 3

140.99 g of acrolein tetramer were added to 58.02 g of dried ethanol containing 0.1% w/w anhydrous ferric chloride. The mixture was then maintained in a sealed vessel at 80° C. for 2.5 hours.

A clear, pale brown oil of density 1.075 g cm$^{-3}$ and viscosity of 130cP at 21° C. resulted. The oil gave no characteristic >C=C< IR absorption at 1645 cm$^{-1}$.

EXAMPLE 4

1.47 g of acrolein tetramer were added to 3.00 g of dried ethanol containing 0.1% w/w anhydrous ferric chloride. The mixture was then maintained in a sealed vessel at 80° C. for 7 hours.

A clear, pale brown oil resulted, which gave no characteristic >C=C< IR absorption at 1645 cm$^{-1}$.

EXAMPLE 5

30.50 g of acrolein tetramer were added to 14.60 g of dried ethanol containing 0.1% w/w anhydrous ferric chloride. The mixture was then maintained in a sealed vessel at 75° C. for 2.5 hours.

A clear, pale brown oil resulted, which gave no characteristic >C=C< IR absorption at 1645 cm$^{-1}$.

EXAMPLE 6

0.415 g of anhydrous ferric chloride was dissolved, at room temperature, in 41.50 g dried ethanol to form a 0.1% w/w solution. 100 g of acrolein tetramer were than gradually added, with stirring, to the ethanolic solution. The clear yellow liquid so formed was first heated for 0.5 hours at 50° to 60° C. and then heated for 3 hours at 80° C. A clear viscous yellow oil resulted which gave no characteristic >C=C< IR absorption at 1645 cm$^{-1}$.

This oil was next purified by first neutralising the acidic catalyst by passage through a basic alumina column and thereafter distilling under vacuum in a Kugalruhr distillation unit to give a clear viscous colourless oil (bp 170° to 175° C. at 0.1mmHG). The product is believed to have the formula:

with which the analysis is consistent:

| | calculated (%) | found (%) |
|---|---|---|
| gravimetric: C | 60.73 | 60.76 |
| H | 8.91 | 9.00 |
| IR: | 1075, 1061 and 1031 cm$^{-1}$: bands of tetrahydropyran | |
| | No bands in the hydroxyl absorption region | |
| | No bands in the olefinic unsaturation absorption region | |
| $^1$H-NMR: | δ 1.1–1.3 | —CH$_3$ |
| | δ 1.5–1.9 | —CH$_2$ - (ring) |
| | δ 3.3.–4.2 | —CH$_2$ - (ester and ethyl) |
| | δ 4.4–4.6) | —CH< |
| | δ 4.8–5.0) | |

EXAMPLE 7

45.39 g of acrolein tetramer were added to 30.00 g of dried n-butanol containing 0.1% w/w anhydrous ferric chloride. The mixture was then maintained, with continuous stirring, at 80° C. for 70 minutes.

A clear, pale brown oil of density 1.020 gcm$^{-3}$ and viscosity of 125CP at 21° C. resulted. The oil gave no characteristic >C=C< IR absorption at 1645 cm$^{-1}$.

EXAMPLE 8

43.39 g of acrolein tetramer were added to 30.00 g of dried butan-2-ol containing 0.1% w/w anhydrous ferric chloride. The mixture, with continuous stirring, was then maintained in a sealed vessel at 80° C. for 4 hours.

The resulting oil gave no characteristic >C=C< IR absorption at 1645 cm$^{-1}$.

EXAMPLE 8

23.10 g of acrolein tetramer were added to 26.90 g of dried n-octanol containing 0.1% w/w anhydrous ferric chloride. The mixture was then maintained in a sealed vessel at 80° C. for 2.5 hours.

A clear, pale brown oil of density 0.96 gcm$^{-3}$ and viscosity of 170CP at 22° C. resulted. The oil gave no characteristic >C=C< IR absorption at 1645 cm$^{-1}$.

EXAMPLE 10

1.72 g of acrolein tetramer were added to 2.00 g of dried n-octanol containing 0.1% w/w p-toluenesulphonic acid. The mixture was then maintained in a sealed vessel at 80° C. for 6 hours.

A clear, pale straw-coloured oil resulted which gave no characteristic >C=C< IR absorption at 1645 cm$^{-1}$.

EXAMPLE 11

16.455 g of acrolein tetramer were added to 27.334 g of melted n-dodecanol containing 0.1% w/w ferric chloride. The mixture was then maintained in a sealed vessel at 80° C. for 4 hours.

A clear, pale brown oil of density 0.944gcm$^{-3}$ and viscosity of 180cP at 22° C. resulted (mp −7° C.). The oil gave no characteristic >C=C< IR absorption at 1645 cm$^{-1}$.

EXAMPLE 12

4.587 g of acrolein tetramer were added to 11.002 g of melted n-octadecanol containing 0.1% w/w ferric chloride. The mixture was then maintained with continuous stirring in a sealed vessel at 100° C. for 0.5 hours.

The solid product (mp 39° C.) gave no characteristic >C=C< IR absorption at 1645 cm$^{-1}$.

EXAMPLE 13

1.252 g of acrolein tetramer were added to 1.111 g of dried cyclohexanol containing 0.1% w/w anhydrous ferric chloride. The mixture was then maintained at 80° C. for 1 hour after which almost complete conversion had occurred; however, after a further 4 hours at 80° C. some IR absorption at 1645 cm$^{-1}$ remained.

EXAMPLE 14

15.3204 g of 1,4-butanediol (ex Aldrich) were mixed with 0.0534 g of anhydrous ferric chloride and left in an over for 2 to 4 hours at 80° C., with occasional stirring, to form a 0.1% w/w solution. 38.1225 g of acrolein tetramer were then added dropwise, with warming and stirring, to the solution at 80° C. and the reaction mixture became homogeneous within a short time. The resulting clear brown, viscous liquid was then maintained at 80° C. for 3 to 4 hours until no characteristic >C=C< IR absorption at 1645 cm$^{-1}$ occurred.

EXAMPLES 15 TO 17

Proceeding in essentially the same manner described in Example 14, 1,4-butanediol and acrolein tetramer were reacted together in the non-stoichiometric ratios shown in Table 1.

TABLE 1

| Example | mole ratio 1,4-butanediol: acrolein tetramer | wt acrolein tetamer (g) | wt 1,4-butanediol (g) | wt anhydrous ferric chloride (g) |
|---|---|---|---|---|
| 15 | 1:1.25 | 38.1225 | 19.108 | 0.0572 |
| 16 | 1:1.50 | 35.8800 | 21.6288 | 0.0575 |
| 17 | 1:1.20 | 29.1525 | 23.4312 | 0.0526 |

EXAMPLES 18 TO 20 proceeding in essentially the same manner as described in Example 14, 1,4-butanediol, ethanol and acrolein tetramer were reacted together in the stoichiometric ratios shown in Table 2.

TABLE 2

| Example | mole ratio acrolein tetramer: 1,4-butanediol: ethanol | Weight acrolein tetramer (g) | Weight 1,4-butanediol (g) | Weight ethanol (g) | Weight anhydrous ferric chloride (g) |
|---|---|---|---|---|---|
| 18 | 3:2:2 | 40.365 | 10.814 | 5.528 | 0.0579 |
| 19 | 2:1:2 | 40.365 | 8.111 | 8.294 | 0.0568 |
| 20 | 3:1:4 | 40.365 | 5.407 | 11.057 | 0.0568 |

EXAMPLE 21

38.250 g of polypropylene glycol 425 (ex Aldrich) were heated to 80° and mixed with 0.0584 g of anhydrous ferric chloride to form a 0.1% w/w solution. 20.183 g of acrolein tetramer were then gradually added dropwise, with warming and stirring, over a period of 0.5 hours. The resulting light yellow, viscous liquid was then maintained at 80° C. until no characteristic >C=C< IR absorption at 1645 cm$^{-1}$ occurred.

EXAMPLES 22 TO 24

Proceeding in essentially the same manner as described in Example 21, polypropylene glycol 425 and acrolein tetramer were heated together in the non-stoichiometric ratios shown in Table 3.

TABLE 3

| Example | mole ratio acrolein tetramer: polypropylene glycol 425 | Weight acrolein tetramer (g) | Weight polypropylene glycol 425 (g) | Weight anhydrous ferric chloride (g) |
|---|---|---|---|---|
| 22 | 1:1.25 | 17.940 | 42.500 | 0.0604 |
| 23 | 1:1.50 | 15.968 | 44.625 | 0.0603 |
| 24 | 1:2.00 | 11.225 | 42.500 | 0.0537 |

EXAMPLE 25

Proceeding in essentially the same manner as described in Example 21, pluronic 72 ($\overline{M}_n$ 2750) and acrolein tetramer were heated together in stoichiometric ratio.

The number average molecular weights ($\overline{M}_n$) and the glass transition temperatures (Tg) of the polymers of Examples 14 to 25 are shown in Table 4.

TABLE 4

| Example | $\overline{M}_n$[a] | Tg °C.[b] |
|---|---|---|
| 14 | 881 | −4 |
| 15 | 819 | −10 |
| 16 | 734 | −17 |
| 17 | 443 | −31 |
| 18 | 1090 | −10 |
| 19 | 670 | −22 |
| 20 | 776 | −35 |
| 21 | 2597 | −29 |
| 22 | 2210 | −36 |
| 23 | 1625 | −42 |
| 24 | 994 | −47 |
| 25 | 5980 | −58 |

[a]Determined by vapour phase osmometry
[b]Determined by DuPont 990 differential scanning calorimeter In the following experiments several derivative oils of this invention, prepared as aforesaid, were evaluated and compared for suitability as matrixes for active substances in the preparation of injectable depot antimalarial systems.

The following key correlates the derivative notation with the preparative Example:

| | | | | | |
|---|---|---|---|---|---|
| S1 | Example 2 | S9 | 24 | S17 | 25 |
| S2 | Example 5 | S10 | 14 | | |
| S3 | Example 9 | S11 | 15 | | |
| S4 | Example 11 | S12 | 16 | | |
| S5 | Example 7 | S13 | 17 | | |
| S6 | Example 8 | S14 | 18 | | |
| S7 | Example 22 | S15 | 19 | | |
| S8 | Example 23 | S16 | 20 | | |

Depot preparations were made up by adding, by hand mixing, powdered active substance to the respective oil at 30% w/w.

EXPERIMENT 1

Twenty-eight groups of mice, 5 mice per group, were selected at random from pooled Tuck TFW male white mice of approximately body weight 20 g. The mice were provided with food and water ad libitum. Care was taken that the diet contained adequate levels of p-aminobenzoic acid and that the mouse stock was free from infection with *Eperythrozoon coccoides*.

On day 0 the groups of mice were processed as follows:

| | |
|---|---|
| Groups (cages) no. 2, 9, 16 & 23 - | all mice received 50 mg S1 subcutaneously (sc) |
| Groups (cages) no. 1, 8, 15 & 22 - | all mice received 50 mg S1 + pyrimethamine (sc) |
| Groups (cages) no. 4, 11, 18 & 25 - | all mice received 50 mg S2 sc |
| Groups (cages) no. 3, 10, 17 & 24 - | all mice received 50 mg S2 + pyrimethamine (sc) |
| Groups (cages) no. 6, 13, 20 & 27 - | all mice received 50 mg S3 sc |
| Groups (cages) no. 5, 12, 19 & 26 - | all mice received 50 mg S3 + pyrimethamine (sc) |
| Groups (cages) no. 7, 14, 21 & 28 - | all mice were employed as untreated controls |

Subcutaneous injections were administered in the mid dorsal, suprascapular position. Cages were examined daily and all deaths recorded. Mice were examined for evidence of local irritation at the site of injection.

On day 7, groups (cages) 1 to 7 inclusive were infected with *Plasmodium berghei* (N strain). 0.2 ml of an inoculum containing $1 \times 10^6$ infected mouse erythrocytes was injected into the tail vein of each recipient mouse. The presence or absence of patent malarial infection was determined by blood film examination three days post infection and at intervals thereafter. Standard procedures were employed in the examination of Giemsa stained blood films and in the determination of parasitaemia levels. On days 21, 32, 45 further groups of mice were infected as shown in Table 5 below. The method of infection and the techniques for assessment of parasitaemia were as described previously. Some groups in which no parasitaemia developed after the initial inoculation with *P. berghei* were subsequently reinfected on the days illustrated in Table 5.

TABLE 5

The time (in days) after injection of derivative oil on which mice were inoculated with *P. berghei* (N strain)

| Time (Day) | Groups (cages inoculated with *P. berghei*) |
|---|---|
| 7 | 1, 2, 3, 4, 5, 6, 7 |
| 21 | 8, 9, 10, 11, 12, 13, 14 |
| 32 | 15, 16, 17, 18, 19, 20, 21 |
| 45 | 22, 23, 24, 25, 26, 27, 28 |
| 48 | 24, 25 |
| 49 | 15, 17 |
| 63 | 22, 24 |

An apparent anomaly in Table 5 is the reinfection of groups 24 and 25 only 3 days after the initial infection with *P. berghei*. These animals were reinfected since on day 3 post-infection no malaria parasite was observed in the blood of any mouse in group 24, which had received S2 + pyrimethamine, or group 25, which had received S2 alone. Group 28, the untreated control group infected on day 45, had a mean parasitaemia of 7.9% on that day and it was assumed that experimental error was responsible for the failure to infect group 25 and/or 24. Group 17, 18 and 21 may be compared with 24, 25 and 28. It should be noted that 3 days after initial infection, Group 18 possessed a mean parasitaemia of 11.6% and in the untreated controls, Group 21, the parasitaemia on that day was 12%.

The results obtained in this experiment are presented in Table 6. At 7 days after injection of the oils + pyrimethamine all three groups of mice, namely Groups 1, 3 and 5, were protected from *P. berghei* challenge, whereas those groups which received oil along, Groups 2, 4 and 6, and Group 7 succumbed to infection.

By 21 days post injection animals which had received S3 + pyrimethamine were not protected against malaria challenge but both S1 + pyrimethamine and S2 + pyrimethamine were still effective.

TABLE 6

The susceptibility to infection with *P. berghei* of mice challenged at varying intervals subsequent to sc injection with pyrimethamine (pyr) in the oil of this invention, or oil alone. Dosages employed are given in the text.

| Group | Dosed with | Interval between drugging and infection (days) | Parasitaemia (%) on (days post infection) | | | |
|---|---|---|---|---|---|---|
| | | | 3 | 7 | 10 | 17 |
| 1 | S1 + pyr | 7 | 0 | 0 | | |
| 2 | S1 | 7 | 9.9 | 80* | | |
| 3 | S2 + pyr | 7 | 0 | 0 | | |
| 4 | S2 | 7 | 11.2 | 80* | | |
| 5 | S3 + pyr | 7 | 0 | 0 | | |
| 6 | S3 | 7 | 10.2 | 80* | | |
| 7 | — | 7 | 8 | | | ns |
| 8 | S1 + pyr | 21 | 0 | 0 | | |
| 9 | S1 | 21 | 16.2 | 80* | | |
| 10 | S2 + pyr | 21 | 0 | 0 | | |
| 11 | S2 | 21 | 24 | 80* | | |
| 12 | S3 + pyr | 21 | 19 | 74* | | |
| 13 | S3 | 21 | 18.8 | 80* | | |
| 14 | — | | 22.2 | 80* | | |
| 15 | S1 + pyr | 32 | 0 | 4 | | 25 |
| 16 | S1 | 32 | 4.8 | 57 | | |
| 17 | S2 + pyr | 32 | 0 | 0 | | 0 |
| 18 | S2 | 32 | 11.6 | 56 | | |
| 19 | S3 + pyr | 32 | 11.2 | 32 | | |
| 20 | S3 | 32 | 12.2 | 72 | | |
| 21 | — | | 12.0 | 38 | | |
| 22 | S1 + pyr | 45 | 2.2 | 20.3 | 40 | |
| 23 | S1 | 45 | 10.3 | 55 | ns | |
| 24 | S2 + pyr | 45, 48 | 0 | 0 | 0 | |
| 25 | S2 | 45, 48 | 0/8.8 | 16.4 | 80 | |
| 26 | S3 + pyr | 45 | 11.7 | 65 | 80 | |
| 27 | S3 | 45 | 10.5 | 81 | 80 | |
| 28 | — | 45 | 7.9 | 82 | 80 | |
| 15 | S1 + pyr | 49 (reinfection) | 6.5 | 49 | | |
| 17 | S2 + pyr | 49 (reinfection) | 0 | 0 | | |
| Control | — | — | 6.8 | 5.0 | | |
| 22 | S1 + pyr | 63 (reinfection) | 6.7 | 40 | | |
| 24 | S2 + pyr | 63 (reinfection) | 0.4 | 0 | | |
| Control | — | — | 30 | 50 | | | ns—no survivors
*estimated prasitaemis. 1 only survivor with marked anaemia and very high parasitaemis.

At 45 days only that group of animals which had been injected with pyrimethamine in S2 (Group 24) were uniformly protected against challenge. In Group 22, 2 out of 4 mice remained negative by blood film examination at 45 days and of the two surviving mice from Group 15 which were reinfected on day 49, only 1 of the 2 developed a parasitaemia. Four mice from Group 24 (S2 + pyrimethamine) were reinfected on day 63. Two of these mice had patent parasitaemias on day 3 post-reinfection but were negative on day 4 and remained negative through the period of examination (11 days).

Mice from Groups 23, 25 and 27 were sacrificed and necropsied 54 days after the injection of 50 mg of S1, S2 and S3, respectively. No evidence of adverse tissue reaction to the oils was evident at the site of injection. The relative amounts of injected oil remaining in individual mice demonstrated that little, if any degradation or dispersion of the oil S3 had occurred in 54 days. No signs of the injected oil were observed in 2 of 4 mice which received S1 and small discrete globules of an opaque brown 'fluid' were observed in the remaining two mice. No obvious tissue reaction was observed at the site of the residual injected material. Residues of the injected material were found in each of the 5 mice which had received S2. The fluid appeared well tolerated with no apparent host reaction.

It should be noted that there is no direct correlation with the duration of effect of pyrimethamine/oil mixtures and the life of the oil itself. S3 appears, from the preliminary observations made above, to persist in vivo for a significantly greater period than S1 or S2 but the period of antimalarial protection afforded by the S3 oil + pyrimethamine was very much shorter than either of the others. S1 appears to persist for, or possess a life expectancy of, approximately 8 weeks and, whilst it was effective with pyrimethamine at three weeks, an intermediate level only was observed at six to seven weeks.

S2 appears to show considerable promise. It appears to be stable for a surprisingly long time in vivo and remained at the site of injection as discrete globules. It also, with pyrimethamine, conferred protection of mice for a minimum period of 9 weeks.

EXPERIMENT 2

This experiment was designed to extend the observation presented above in Experiment 1. All basic experimental procedures, including the preparation of 30% w/w dispersions of pyrimethamine base in S1, S2 and S3, were performed as described above. The primary objective was to obtain confirmation of the results obtained above whilst extending the period of observation. Since no adverse host reactions were observed to the oils (without pyrimethamine) and since they also lack any antimalarial activity the experimental design was simplified by including only S2 as an oil with antimalarial compound. Twenty-seven groups of mice, with 5 mice in each, were again selected at random from pooled male white mice (Tuck TFW) of 20 gm body weight. Individual groups received 50 mg injections sc of S1 + pyrimethamine, S2 + pyrimethamine, S3 + pyrimethamine or S2 above. The distribution of groups is shown below:

| Inoculum | Groups |
| --- | --- |
| S1 + pyrimethamine | 1, 6, 11, 16, 20, 24 |
| S2 + pyrimethamine | 2, 7, 12, 17, 21, 25 |
| S3 + pyrimethamine | 3, 8, 13 |
| S2 − | 4, 9, 14, 18, 22, 26 |
| Control, untreated | 5, 10, 15, 19, 23, 27 |

At intervals of 14 days one group of mice from each of the different classes of inocula were infected by the intravenous injection of 1×10⁶ mouse erythrocytes parasitised with *P. berghei* (N strain). Details are given in Table 7.

TABLE 7

The time (in days) after injection of derivative oil and pyrimethamine mixtures at which mice were infected with *Plasmodium berghei* (N strain)

| Time (days) | Groups (cages) of mice infected with *P. berghei* |
| --- | --- |
| 14 | 1, 2, 3, 4, 5, |
| 28 | 6, 7, 8, 9, 10 |
| 42 | 11, 12, 13, 14, 15 |
| 56 | 16, 17, 18, 19 |
| 70 | 20, 21, 22, 23 |

TABLE 7-continued

The time (in days) after injection of derivative oil and pyrimethamine mixtures at which mice were infected with *Plasmodium berghei* (N strain)

| Time (days) | Groups (cages) of mice infected with *P. berghei* |
| --- | --- |
| 84 | 24, 25, 26, 27 |

The examination of mice for *P. berghei* infection was performed as described above in Experiment 1. The results are presented in Table 8. These results demonstrate that 50 mg of the oil S2, containing a 30% w/w/ dispersion of pyrimethamine base, when injected sc in mice afforded antimalarial protection for not less than 12 weeks.

S1 + pyrimethamine protected mice for between 6 to 8 weeks but high mortality rates were obtained in some groups which received this mixture. S3 + pyrimethamine protected mice for less than 2 weeks.

The experiment is considered adequately to confirm the efficacy of S2 as a matrix for pyrimethamine in the preparation of injectable sustained-release antimalarial systems.

TABLE 8

The susceptibility to infection with *P. berghei* of mice challenged at varying times subsequent to injection sc with pyrimethamine (pyr) in derivative oil or with oil alone
The dosages employed are given in the text.

| Group | Dosed with | Day of challenge | Parasitaemia on (days post infection) | | |
| --- | --- | --- | --- | --- | --- |
| | | | 3 | 5 | 10 |
| 1 | S1 + pyr | 14 | 0 | 0 | 0 |
| 2 | S2 + pyr | 14 | 0 | 0 | 0 |
| 3 | S3 + pyr | 14 | 50[a] | 71[a] | |
| 4 | S2 | 14 | 41 | 80[a] | |
| 5 | — | 14 | 32 | 82 | |
| 6 | S1 + pyr | 28 | 0 | 0 | 0 |
| 7 | S2 + pyr | 28 | 0 | 0 | 0 |
| 8 | S3 + pyr | 28 | —[b] | —[b] | —[b] |
| 9 | S2 | 28 | 26 | 50 | |
| 10 | — | 28 | 28 | 66 | |
| 11 | S1 + pyr | 42 | 0 | 0 | 0 |
| 12 | S2 + pyr | 42 | 0 | 0 | 0 |
| 13 | S3 + pyr | 42 | —[b] | —[b] | —[b] |
| 14 | S2 | 42 | 3.7 | 32 | |
| 15 | — | 42 | 2.3 | 23 | 63 |
| 16 | S1 + pyr | 56 | 0.2 | 23 | 62 |
| 17 | S2 + pyr | 56 | 0 | 0 | 0 |
| 18 | S2 | 56 | 26 | 70 | 78 |
| 19 | — | 56 | 24 | 62 | 76 |
| 20 | S1 + pyr | 70 | —[b] | —[b] | —[b] |
| 21 | S2 + pyr | 70 | 0 | 0 | 0 |
| 22 | S2 | 70 | 23 | 74 | 80[a] |
| 23 | — | 70 | 19 | 68 | 80 |
| 24 | S1 + pyr | 84 | 4.5 | 33 | |
| 25 | S2 + pyr | 84 | 0 | 0.02[c] | 0 |
| 26 | S2 | 84 | 29.6 | 70 | 80 |
| 27 | — | 84 | 31 | 68 | 80 |

[a]only one mouse surviving in the group
[b]all mice dead prior to challenge
[c]one mouse of 5 patent (parasitaemia 0.1% day 8)

EXPERIMENT 3

This experiment was designed to extend, in relation both to other derivatives and other active substances, the observations presented above. All basic experimental procedures were as described above except that the *P. berghei* challenge was presented at 7, 14, 28, 42, 56 and 84 days after administration of active substance.

The results are presented in Table 9.

TABLE 9

| Derivative oil | Minimum duration of protection (days) with: | | |
|---|---|---|---|
| | pyrimethamine (free base) | Sulphadiazine | Sulphadoxine |
| S1 | 42 | 14 < 28 | <14 |
| S2 | 84 | 70 < 84 | <28 |
| S3 | <7[a] | 56 < 70 | <14 |
| S4 | <28[a] | <14 | <28 |
| S5 | 28 < 56[a] | 42 | <28 |
| S6 | 28 < 56[a] | 42 | <28 |

[a]Acute toxicity was associated with administration of this mixture.

These results demonstrate that no significantly prolonged duration of the effect of sulphadoxine was obtained with any of the oils tested. Sulphadiazine gave extended protection when blended with each of the oils, with the exception of S4.

Pyrimethamine gave extended protection with all oils except S3 and S4. The greatest duration of protection was obtained with S2. The injection of pyrimethamine blended in oils S3, S4, S5 and S6 was associated with manifestations of severe acute toxicity which was sometimes fatal. This aspect is discussed further below.

Toxicity and Tissue Irritability of the Derivative Oils

An extensive toxicological investigation of the oils, either alone or in combination with antimalarials, has not been undertaken. The observations reported here are based on the behaviour and condition of mice immediately following injection of test substances, and on the development of any obvious gross pathology subsequent to drugging. All animals in experimental groups were examined at intervals for evidence of ulceration or other tissue reactions at the site of injection and mice were killed at intervals and examined for residual oil deposits and evidence of adverse tissue reactions to such deposits.

Not one of the oils studied, when administered without drug, induced any apparent acute of chronic reaction in mice. Immediately following injection, even at 100 mg/mouse, the animals were normal in their behaviour and no adverse reaction was noted. The oils were extremely well tolerated by the tissues, no evidence of adverse reaction to any oil being observed.

Animals which received the oils with either sulphadiazine or sulphadoxine likewise developed no adverse response to the mixtures, either immediately after injection or on long-term observation.

No adverse response was observed to 50 mg blends of pyrimethamine with S1 or S2 but when 100 mg of either blend was employed 1/5 mice died by 24 hours although no symptoms of acute toxicity were observed by 6 hours after drugging. A severe toxicosis developed within a short interval of the administration of 50 mg of 30% pyrimethamine with each of the other oils (S3, S4, S5 and S6). This toxicosis was first clearly evident 4 hours after drugging, the mice appearing distressed and hyperactive with erratic movement. Later mice collapsed, their limbs jerking. Bleeding from the mouth resulted from the tongue being protruded and bitten by the mouse. One mouse from each of the groups dosed with S3, S4 and S5 + pyrimethamine was dead at 24 hours but all surviving mice were normal and showed no persistent drug effect. 100 mg dosages of S3, S4, S5 and S6 + pyrimethamine proved highly toxic to mice and all mice which received these blends were dead within 24 hours (2 mice from each of the groups with S4, S5 and S6 + pyrimethamine were euthanised 6 hours after drugging since they were in great distress).

The behavioural signs of drug toxicity were even more pronounced in these groups than in those which received 50 mg doses of the blends.

The effects described above were not observed in mice which received pyrimethamine base in an aqueous suspension at doses of either 15 mg or 30 mg/mouse (750 and 1500 mg/kg). One of 5 mice which received pyrimethamine base at 1500 mg/kg was dead at 24 hours. It is presumed that the base is released from some oils at a greater rate than from depots of powdered drug in water. This effect may reflect the degree of solubility of pyrimethamine base in the oils, a conclusion supported by studies with pyrimethamine isethionate. When administered sc at dosages equivalent to 750 mg/kg and 1500 mg/kg base, the isethionate induced distress in animals within minutes and all mice died within 1 hour of dosing.

Mice which received 50 mg of pyrimethamine base in S3, S4, S5, and S6, and survived to 24 hours appeared normal and showed no further evidence of reaction to the oil + drug.

None of the oils tested, alone or with pyrimethamine base, sulphadiazine or sulphadoxine gave rise to visible signs of chronic tissue irritation. There was no hair loss, swelling, or signs of inflammatory reaction in the skin at the site of injection and the mice were normal to handle, giving no indication of tenderness at that site. Evidence that the oils were well tolerated was also obtained from autopsy. At 54 days after administration of oils mice were killed, the skin from the dorsal surface of the thorax removed and the connective tissue examined.

Of the oils tested the S1 preparation was the least durable in vivo. At 8 weeks no visible residues were found in some mice and in the remainder small, dark brown deposits at the injection site represented the residue. The duration of protection afforded mice by pyrimethamine S1 mixtures correlates with the life of the matrix, no mouse with this preparation being protected to 8 weeks.

Somewhat greater quantities, albeit small amounts, of S2 were visible in mice at 54 days. The oil appeared hyaline and light brown and there was no marked fibrosis or vascularisation of the oil depot site.

With each of the S3, S4, S5 and S6 preparations greater residual masses were obtained at 54 days than with the S2 preparation. The oils appeared unchanged and had elicited no appreciable host tissue reaction. S3 + pyrimethamine protected mice for less than 7 days and this, together with the acute toxicosis observed after injection of the oil/drug blend is consistent with an extremely rapid release of drug from the oil in vivo. The intermediate periods of antimalarial protection provided by pyrimethamine in S4, S5 and S6 indicate that the release of pyrimethamine in these oils is slower than from S3 but there is presumably still an extremely rapid drug loss after dosing.

Combined Pyrimethamine and Sulphadiazine Preparations

The encouraging results obtained with both pyrimethamine and sulphadiazine in oil S2 indicated that these systems could be exploited for studies on the release of drug mixture from a single oil depot. As a preliminary step 10% pyrimethamine-base-S2 mixtures were evaluated and it was shown that 50 mg of 10% pyrimethamine in S2 injected sc gave at least three months protection in mice.

EXPERIMENT 4

This experiment was designed to ascertain whether the sustained release composition of this invention could be utilised for the release of a mixture of active substances from a single depot. Preparations of 30% sulphadiazine + 10% pyrimethamine base in S2 (a new batch prepared as in Example 6) were blended and injected sc in 50 mg aliquots into mice in the suprascapular position. Additional groups of mice received S2 alone or no drug. Three groups of mice with S2 + drugs and 1 group with S2 alone were prepared for challenge on each of days 28, 42, 56 and 70. At each time interval one group each of the S2 + drug mice were challenged by the inoculation iv of $1 \times 10^6$ mouse erythrocytes infected with the drug sensitive N strain of *P. berghei*, the pyrimethamine resistant PYR strain and the sulphonamide resistant ORA strain, respectively. The group of mice with S2 alone was challenged with N strain parasites. Additional groups of control mice without oil were dosed with pyrimethamine (60 mg/kg) and orisulf (1000 mg/kg) immediately post-infection.

The results obtained in this experiment are summarised in Table 10 below.

The results of this experiment showed that 4 weeks after the injection of S2 containing a mixture of pyrimethamine and sulphadiazine, all mice challenged were protected against drug sensitive, pyrimethamine and sulphonamide resistant parasites. At 6 weeks one mouse in each of the groups challenged with N, PYR and ORA strains respectively, developed a parasitaemia but at 8 weeks, 4 of 5, 4 of 5 and 2 of 4 mice challenged with the N, PYR and ORA strains respectively were susceptible to challenge. A residual drug effect at 8 weeks was however demonstrated by the slowness with which parasitaemia developed in cage 8 mice where, following N strain challenge a parasitaemia (0.5%) was observed in only a single mouse on day 3. The day 3 N strain parasitaemias in control cages 4, 5 and 11 were 15.3, 25.8 and 9.0 respectively, with 15/15 mice patent.

Ancillary tests were then initiated to determine the duration of effect as sulphadiazine (30%) and pyrimethamine (10%) in S2. The results of these tests and comparison with the results obtained with the combination of the drugs in shown in Table 11 below.

TABLE 11

The duration of effect of pyrimethamine, sulphadiazine and a combination of the two drugs in S2 when administered to mice sc as 50 mg or 100 mg of oil/drug blend. Mice were challenged with N strain *P. berghei* and examined for parasitaemia for 14–17 days after challenge

| Drug and % composition | Dosage of oil drug blend (mg) | Number of mice developing parasitaemia after challenge on day: | | | |
|---|---|---|---|---|---|
| | | 14 | 28 | 42 | 56 |
| pyrimethamine (10%) + sulphadiazine (30%) | 50 | 0/5 | 0/5 | 1/4 | 5/5 |
| pyrimethamine (10%) | 50 | 0/5 | 0/5 | 4/5 | |
| sulphadiazine (30%) | 50 | 0/5 | 0/5 | 4/5 | |
| sulphadiazine (30%) | 100 | 0/4 | 0/4 | 4/5 | |

As noted above, the rate of development of parasitaemia in mice with the drug combination in S2 demonstrated that a residual drug effect was present at day 56 but Table 11 shows that there was a very clear difference in the degree of protection in mice with pyrimethamine and sulphadiazine and in those with the drug combination. 50 mg and 100 mg of S2 containing 30% sulphadiazine fully protected mice against N strain challenge at days 14 and 28. A failure of protection occurred by day 42 however, with 4/5 mice on both regimens patent by day 3 post infection. 10% pyrimethamine in 50 mg S2 likewise protected mice against N strain challenge on days 14 and 28 but by day 42 4 of 5 mice were patent on day 3 of infection. If earlier results obtained with the first batch of S2 are excluded from this study then the results of this experiment with the drug combination are encouraging since it appears that pyrimethamine + sulphadiazine together exert a greater and more prolonged antimalarial effect than either drug singly.

EXPERIMENT 5

This experiment (which is incomplete) was designed to ascertain the suitability of the derivatives of this invention in the administration of antibiotics. All basis experimental procedures were as described above except that the mice received 100 mg of the 30% mixtures of active substance (tetracycline as free base, or tetracycline as hydrochloride).

TABLE 10

The duration of protection against drug sensitive (N strain) pyrimethamine-resistant (PYR strain) and sulphonamide-resistant (ORA strain) *P. berghei* afforded mice by 50 mg subcutaneous depots of derivative oil S2 containing 30% sulphadiazine and 10% pyrimethamine.

| Cage No | Drug preparation | Time of challenge (days post-drugging) | Strain of challenge | Mice with patent parasitaemia post-challenge days: | | | | |
|---|---|---|---|---|---|---|---|---|
| | | | | 3 | 7 | 10 | 14 | 17 |
| 1 | S2 + sulph + pyr | 28 | N | 0 | 0 | | 0 | |
| 2 | S2 + sulph + pyr | 28 | PYR | 0 | 0 | | 0 | |
| 3 | S2 + sulph + pyr | 28 | ORA | 0 | 0 | | 0 | |
| 4 | S2 | 28 | N | 5/5 | 5/5 | | | |
| 5 | S2 | 42 | N | 5/5 | 2/2 | | | |
| 1 | | 42 (rechallenge) | N | 0/4 | 1/4 | | 1/4 | |
| 2 | | 42 (rechallenge) | PYR | 0/5 | 0/5 | | 1/5 | |
| 3 | | 42 (rechallenge) | ORA | 0/5 | 4/5 | 1/4 | 2/4 | |
| 6 | pyr (1 × 60 mg/kg) | 0 (day 42 of exp) | PYR | 5/5 | 4/4 | 4/4 | | |
| 7 | orisulf (1 × 1000 mg/kg) | 0 (day 42 of exp) | ORA | 5/5 | 5/5 | 5/5 | | |
| 8 | S2 + sulph + pyr | 56 | N | 1/5 | 5/5 | | | |
| 9 | S2 + sulph + pyr | 56 | PYR | 3/5 | 3/4 | | | |
| 10 | S2 + sulph + pyr | 56 | ORA | 2/4 | 2/4 | | | |
| 11 | S2 | 56 | N | 5/5 | 5/5 | | | |

The results are summarised in Table 12.

TABLE 12

Duration of protection against *P. berghei* infection afforded mice by 30% mixtures of tetracycline free base or hydrochloride in derivative oils. Each mouse received 100 mg of mixture subcutaneously.

| Oil | Tetracycline | Duration of protection (days) |
|---|---|---|
| S1 | free base | 7 < 17 |
|    | HCl | <7 |
| S3 | free base | <7 |
|    | HCl | <7 |
| S2 | free base | 7 < 17 |
|    | HCl | <7 |
| S4 | free base | <17 |
|    | HCl | <7 |
| S5 | free base | <7 |
|    | HCl | <7 |
| S6 | free base | 7 < 17 |
|    | HCl | <7 |

A conspicuous feature of these results was the greater duration of protection afforded mice with tetracycline free base compared with the hydrochloride, in oils S1, S2, S3 and S6. The greatest duration of effect was obtained with oil S2 and tetracycline base.

With all preparations tissue necrosis, with ulceration of the dermal tissues, occurred at the injection site. These lesions were more pronounced in animals which received the hydrochloride.

EXPERIMENT 6

This experiment (which is incomplete) was designed to ascertain the suitability of the polymeric derivatives of this invention in formulating sustained release compositions. All basic experimental procedures were as described above except that the mice received 10 mg of the 30% mixture of active substance (pyrimethamine).

The results are summarised in Table 13.

TABLE 13

| Preparation | Acute toxicity observations | Duration of protection against *P. berghei* challenge (days) |
|---|---|---|
| pyrimethamine + S7 | 16/25 mice dead by 3 days | ><35 |
| pyrimethamine + S8 | 16/25 mice dead by 3 days | ><35 |
| pyrimethamine + S9 | 16/25 mice dead by 3 days | ><35 |
| pyrimethamine + S10 | 1/10 mice dead by 6 days | >21 |
| pyrimethamine + S11 | 0/10 mice dead by 12 days | >21 |
| pyrimethamine + S12 | 3/10 mice dead by 3 days | >21 |
| pyrimethamine + S13 | 5/10 mice dead by <1 day | >21 |
| pyrimethamine + S14 | 0/10 mice dead by 12 days | >21 |
| pyrimethamine + S15 | 0/10 mice dead by 12 days | >21 |
| pyrimethamine + S16 | 0/10 mice dead by 12 days | >21 |
| pyrimethamine + S17 | 4/10 mice dead by 3 days | +N 21 |

S11, S14, S15 and S16 all appear to be of promise.

As to the derivatives per se, each of the polymers tested was well tolerated by the mice. In no instance was evidence found of acute or chronic toxicity in mice which received 100 mg oil by sc injection. No acute tissue reaction was observed with any oil and autopsy examination at 7 days revealed no evidence of significant inflammatory reaction at the site of the oil depot.

Each of the oils S7, S8 and S9 (the only ones on which longer term observations have been made) persisted, as pure compounds, for at least 56 days; at 56 days the oil depot was encapsulated in a thin-walled fibrous 'sac'. The effect of mixing pyrimethamine with the oils apparently reduces their persistence since neither residue of oil in drug was evident after 41 days.

We claim:

1. A sustained release injectable composition, which comprises:
    (i) pyrimethamine and (ii) a monomeric liquid adduct prepared by reacting acrolein tetramer with ethanol.

2. A sustained release composition, which comprises:
    (i) a biologically active substance and (ii) a monomeric liquid compound which is an injectable vehicle, and is obtainable by reacting, if required, in the presence of a Bronsted or Lewis acid:
    (a) at least one acidic, neutral or amphoteric organic compound which contains one, two or a plurality of active hydrogen atom-containing groups and which may be saturated or unsaturated with the, or at least one of the, olefinic bonds of:
    (b) at least one olefinically unsaturated cyclic ether of the formula:

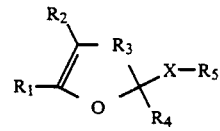

in which $R_1$, $R_2$ and $R_4$, which may be the same or different, with each representing a hydrogen atom or a hydrocarbyl or hydrocarbyloxy group, optimally halo substituted;

$R_3$ represents a methylene, ethylene or 1,3-propylene group;

$R_5$ represents a monovalent group reactive with the organic compound (a) or a hydrogen atom or a $C_1$ to $C_4$ alkyl group; and X represents:

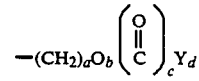

in which Y represents an oxygen atom or an $-NR_6-$ group, wherein $R_6$ represents any of the values which $R_1$ may assume:

a is 0 or 1;
b is 0 or 1;
c is 1 or 2;
d is 0 or 1;

with the proviso that at least one b or d is 1.

3. The composition according to claim 2 wherein (a) is saturated.

4. The composition according to claim 2 wherein (a) is an organic compound containing one, two or a plurality of carboxy, hydroxy, amido or mercapto groups.

5. The composition according to claim 2 wherein (a) is mono-, carboxy or hydroxy aliphatic hydrocarbyl with less than 18 carbon atoms; or di-carboxy or hydroxy aliphatic hydrocarbylene with less than 18 carbon atoms; or n-octadecanol.

6. The composition according to claim 4 wherein (a) is a $C_2$ to $C_4$ alkanol or alkandiol.

7. The composition according to claim 2, wherein at least one of $R_1$, $R_2$ or $R_4$ represents a hydrogen atom.

8. The composition according to claim 2, wherein $R_3$ represents a mono- or poly-substituted or unsubstituted ethylene group.

9. The composition according to claim 2, wherein X represents —COO— or —$CH_2OCO$—.

10. The composition according to claim 2, wherein (b) has the formula:

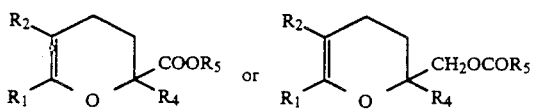

in which $R_1$, $R_2$, $R_4$ and $R_5$ are as defined in claim 2 or 8.

11. The composition according to claim 10 wherein (b) has the formula:

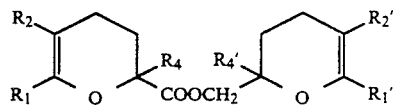

in which $R_1'$, $R_2'$ and $R_4'$ which may be the same or different, represent any of the values which $R_1$, $R_2$ and $R_4$ respectively may assume.

12. The composition according to claim 11, wherein (b) is acrolein tetramer.

13. The composition according to claim 2, wherein the active substance (i) is intimately admixed with the compound (ii).

14. The composition according to claim 2, which is a suspension, dispersion or solution.

15. The composition according to claim 2, wherein the biologically active substance comprises pyrimethamine.

16. The composition according to claim 2, wherein at least part of organic compound (a) comprises a mono-, di- or poly-carboxy, hydroxy or mercapto substituted biologically active compound (i).

* * * * *

UNITED STATES PATENT AND TRADEMARK OFFICE
CERTIFICATE OF CORRECTION

PATENT NO. : 5,096,896
DATED : MARCH 17, 1992
INVENTOR(S) : NEIL B. GRAHAM et al

It is certified that error appears in the above-identified patent and that said Letters Patent is hereby corrected as shown below:

Column 1, line 31, "in particularly," should read --in particular,--.

Column 2, line 6, "utilise unsubstituted" should read --utilize unsubstituted--;
    line 9, "to utilise aliphatic" should read --to utilize aliphatic--;
    line 21, "polymeric, Where" should read --polymeric. Where--;
    line 61, "Examples or" should read --Examples of--.

Column 3, line 9, "acid, b" should read --acid,--.

Column 6, line 31, "the mono" should read --The mono--.

Column 7, line 34, "X represents a" should read --Z represents a--.

Column 8, line 19, "typically 11-300" should read --typically 100-300--.

UNITED STATES PATENT AND TRADEMARK OFFICE
CERTIFICATE OF CORRECTION

PATENT NO. : 5,096,896
DATED : MARCH 17, 1992
INVENTOR(S) : NEIL B. GRAHAM et al

It is certified that error appears in the above-identified patent and that said Letters Patent is hereby corrected as shown below:

Column 9, line 21, "utilised in" should read --utilized in--.

Column 10, line 8, "utilised." should read --utilized--.

Column 12, line 47, "either or" should read --either of--;
line 50, "substance, s" should read --substance as--;
line 58, "catalyst;" should read --catalyst.--.

Column 14, line 19, "3.3.-4.2" should read --3.3-4.2--;
line 20, "4.6)" should read --4.6--;
line 21, "5.0)" should read --5.0--;
line 41, "EXAMPLE 8" should read --EXAMPLE 9--;
line 62, "w/w ferric" should read --w/w anhydrous ferric--.

UNITED STATES PATENT AND TRADEMARK OFFICE
CERTIFICATE OF CORRECTION

PATENT NO. : 5,096,896
DATED : MARCH 17, 1992
INVENTOR(S) : NEIL B. GRAHAM et al

It is certified that error appears in the above-identified patent and that said Letters Patent is hereby corrected as shown below:

Column 15, line 4, ""w/w ferric" should read --w/w anhydrous ferric--;

line 20, "over for 2 to 4" should read --oven for 2 to 4--;

line 46, "proceeding in" should read --Proceeding in--.

Column 16, line 68, "of approximately" should read --of approximate--.

Column 18, line 67, "little, if any" should read --little, if any,--.

Column 19, line 23, "protection of mice" should read --protection on mice--.

Column 20, line 13, "30% w/w/" should read --30% w/w--;

line 28, "with oil alone" should read --with oil alone.--.

Column 23, line 23, "are summarised" should read --are summarized--.

UNITED STATES PATENT AND TRADEMARK OFFICE
CERTIFICATE OF CORRECTION

PATENT NO. : 5,096,896
DATED : MARCH 17, 1992
INVENTOR(S) : NEIL B. GRAHAM et al

It is certified that error appears in the above-indentified patent and that said Letters Patent is hereby corrected as shown below:

Column 24, line 9, "oil drug" should read --oil-drug--; lines 11-15,

"
| | | | | |
|---|---|---|---|---|
| pyrimethamine (10%) + sulphadiazine (30%) | 50 | 0/5 | 0/5 | 1/4 | 5/5 |
| pyrimethamine (10%) | 50 | 0/5 | 0/5 | 4/5 |
| sulphadiazine (30%) | 50 | 0/5 | 0/5 | 4/5 |
| sulphadiazine (30%) | 100 | 0/4 | 0/4 | 4/5 |
"

should read

--
| | | | | |
|---|---|---|---|---|
| pyrimethamine (10%) + sulphadiazine (30%) | 50 | 0/5 | 0/5 | 1/4 | 5/5 |
| pyrimethamine (10%) | 50 | 0/5 | 0/5 | 4/5 |
| sulphadiazine (30%) | 50 | 0/5 | 0/5 | 4/5 |
| sulphadiazine (30%) | 100 | 0/4 | 0/4 | 4/5 |
--;

line 64, "All basis" should read --All basic--.

Column 26, line 32, "optimally halo" should read --optionally halo--.

UNITED STATES PATENT AND TRADEMARK OFFICE
CERTIFICATE OF CORRECTION

PATENT NO. : 5,096,896
DATED : MARCH 17, 1992
INVENTOR(S) : NEIL B. GRAHAM et al

It is certified that error appears in the above-identified patent and that said Letters Patent is hereby corrected as shown below:

Column 27, line 20, "in claim 2" should read --in claim 7--.

Signed and Sealed this

Fourth Day of April, 1995

Attest:

BRUCE LEHMAN

Attesting Officer

Commissioner of Patents and Trademarks